United States Patent [19]

Lisa et al.

[11] Patent Number: 5,252,765
[45] Date of Patent: Oct. 12, 1993

[54] PROCESS FOR PREPARING SULFOPHENYLALKYLSILOXANE OR SULFONAPHTHYLALKYLSILOXANE

[75] Inventors: Rudolph E. Lisa, Grosse Ile, Mich.; Klaus Hilligardt, Limburgerhof; Ulrich M. Kalck, Neuhofen, both of Fed. Rep. of Germany

[73] Assignee: BASF Corporation, Parsippany, N.J.

[21] Appl. No.: 968,030

[22] Filed: Oct. 29, 1992

[51] Int. Cl.$^5$ .............................. C07F 7/08; C07F 7/18
[52] U.S. Cl. .................................................... 556/428
[58] Field of Search ......................................... 556/428

[56] References Cited

U.S. PATENT DOCUMENTS

| | | | |
|---|---|---|---|
| 4,575,559 | 3/1986 | Pauek et al. | 556/428 |
| 5,091,548 | 2/1992 | Davis et al. | 556/428 |
| 5,113,001 | 5/1992 | Welch et al. | 556/428 |

Primary Examiner—Paul F. Shaver

[57] ABSTRACT

Disclosed is a solventless process for the manufacture of sulfophenylalkylsiloxane or sulfonaphthylalkylsiloxanes, wherein the reaction between chlorosulfonic acid and a phenylalkyltrichlorosilane or a naphthylalkyltrichlorosilane is conducted in a reactor containing a self-cleaning agitator to deliver the sulfophenylalkylsiloxane or sulfonaphthylalkylsiloxane in the form of a powder.

10 Claims, 1 Drawing Sheet

PROCESS FOR PREPARING SULFOPHENYLALKYLSILOXANE OR SULFONAPHTHYLALKYLSILOXANE

FIELD OF THE INVENTION

The present invention is directed to a solventless process for production of sulfophenethylsiloxane or sulfonaphthylethylsiloxanes, more specifically it is directed to a solventless process where the reaction is conducted in a reactor containing a self-cleaning agitator to deliver the sulfophenethylsiloxane or sulfonaphthylethylsiloxanes in form of a powder.

BACKGROUND OF THE INVENTION

Sulfophenethylsiloxane or sulfonaphthethylsiloxane and processes for their production are known. The U.S. Pat. No. 2,968,643 describes a reaction of chlorosulfonic acid and a phenyltrichlorosilane to form an intermediate followed by hydrolysis of this intermediate. However, an excess of chlorsulfonic acid is used which has to be separated. The U.S. Pat. No. 4,575,559 discloses a process for the production of sulfophenethylsiloxanes in the presence or absence of solvent. The solventless process in a stirred vessel is technically very difficult because the reaction mixture becomes solid. For this reason most examples use solvents, which must subsequently be removed.

The U.S. Pat No. 5,091,548 discloses a solventless process for the production of sulfophenethylsiloxanes or sulfonaphthylethylsiloxanes, wherein the reaction takes place in small droplets or in a thin film to avoid the handling of the solid intermediate in bulk form.

Object of the present invention was to provide a process for preparing sulfophenylalkylsiloxanes or sulfonaphthylalkylsiloxane which overcomes the problems of handling the solid intermediate and which avoids the use of a solvent. Another object was to provide the phenylalkylsiloxanes or sulfonaphthylalkyl-siloxanes in form of a powder.

SUMMARY OF THE INVENTION

The objects of the present invention could be achieved with a process for preparing a sulfophenylalkylsiloxane or a sulfonaphthylalkylsiloxane having either of the following formulae:

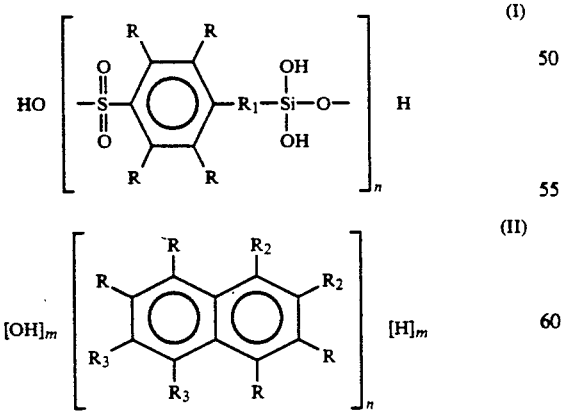

in a reactor containing a self-cleaning agitator, comprising:

a) adding an essentially equimolar ratio of chlorosulfonic acid to a phenylalkyltrichlorosilane or a naphthylalkyltrichlorosilane having either of the following formulae:

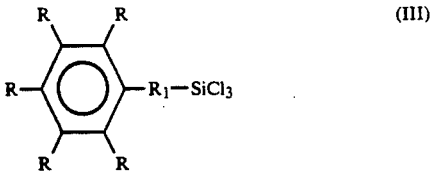

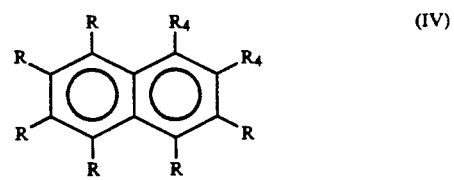

wherein R of formulae I,II,III, and IV is individually hydrogen halogen, or an alkyl radical having 1 to 4 carbon atoms; R1 is an alkylene radical having 2 to 5 carbon atoms; R2 is R or

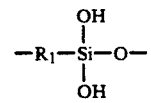

with the proviso that at least one $R_2$ be

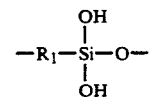

$R_3$ is—H or

with the proviso that at least one $R_3$ be

$R_4$ is R or—$R_1SiCl_3$ with the proviso that at least one $R_4$ be—$R_1SiCl_3$ and n is at least 1, preferably 2 to 4 m is 1 or 2 in said reactor under agitation at a temperature of from about 20° to about 80° C. and at a rate sufficient to control the formation of HCl;

b) raising the temperature up to about 80° to about 150° C. until HCl formation stops and a solid intermediate is formed;

c) optionally reducing the pressure in the reactor to about 300 to about 20 mbar;

d) hydrolyzing the intermediate by adding water in the reactor at a temperature of from about 20° C. to about 50° C. to form said sulfophenylalkylsiloxane or sulfonaphthylalkylsiloxanes and HCL;

e) reducing the pressure in the reactor to about 300 mbar to about 20 mbar at a temperature of from about 20° C. to about 95° C. until excess water and HCl is removed; and f) removing the dry sulfophenylalkylsiloxane or sulfonaphthylalkylsiloxane from the reactor.

DETAILED DESCRIPTION OF THE INVENTION

The phenethyltrichlorosilane and naphthylethyltrichlorosilane compounds having structural formula III and IV are well known in the art.

R is hydrogen, halogen or an alkyl radical having 1–4 carbon atoms, $R_1$ is an alkylene radical having 2 to 5 carbon atoms and $R_3$ is R or—$R_1SiCl_3$ with the proviso that at least one $R_3$ be—$R_1SiCl_3$.

Suitable examples of these compounds are $\beta$-phenethyltrichlorosilane, $\alpha$-phenethyltrichlorosilane and naphthylethyltrichlorosilane.

In the process for preparing the sulfophenethylsiloxane or sulfonaphthylethylsiloxane a reactor containing a self-cleaning agitator is used. The reactor must be suitable for handling paste and solid phases as well as high corrosive materials and the mixing elements must be in an order that they are self cleaning, which means that there are is virtually no dead space between the mixing elements themselves and the reactor walls. One suitable reactor is a so called "all phase" reactor which is commercially available under the trademark Discotherm TM B (List, Pratteln, Switzerland).

FIG. 1 shows a side view of the Discotherm TM B.

FIG. 2 shows a front view of a cut of the Discotherm TM B.

BRIEF DESCRIPTION OF THE FIGURES

The shell of the reactor consists of a double jacket (1). Inside the double jacket is a hollow shaft (2) with discs (3) containing kneading units (4).

Counter paddles (5), paired to the kneading units (4), are located on the inside of the walls of the double jacket (1) and fixd on the walls of the double jacket (1). These stationary units clean the agitator shaft and discs resulting in high efficiency mixing, while rendering the unit to be about 90% self cleaning.

Figure 2:
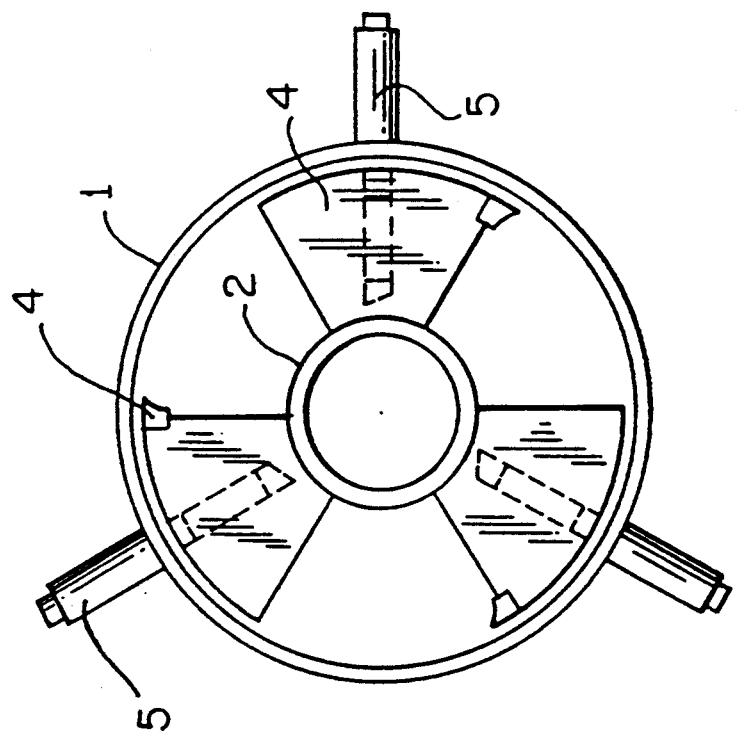
Figure 1:
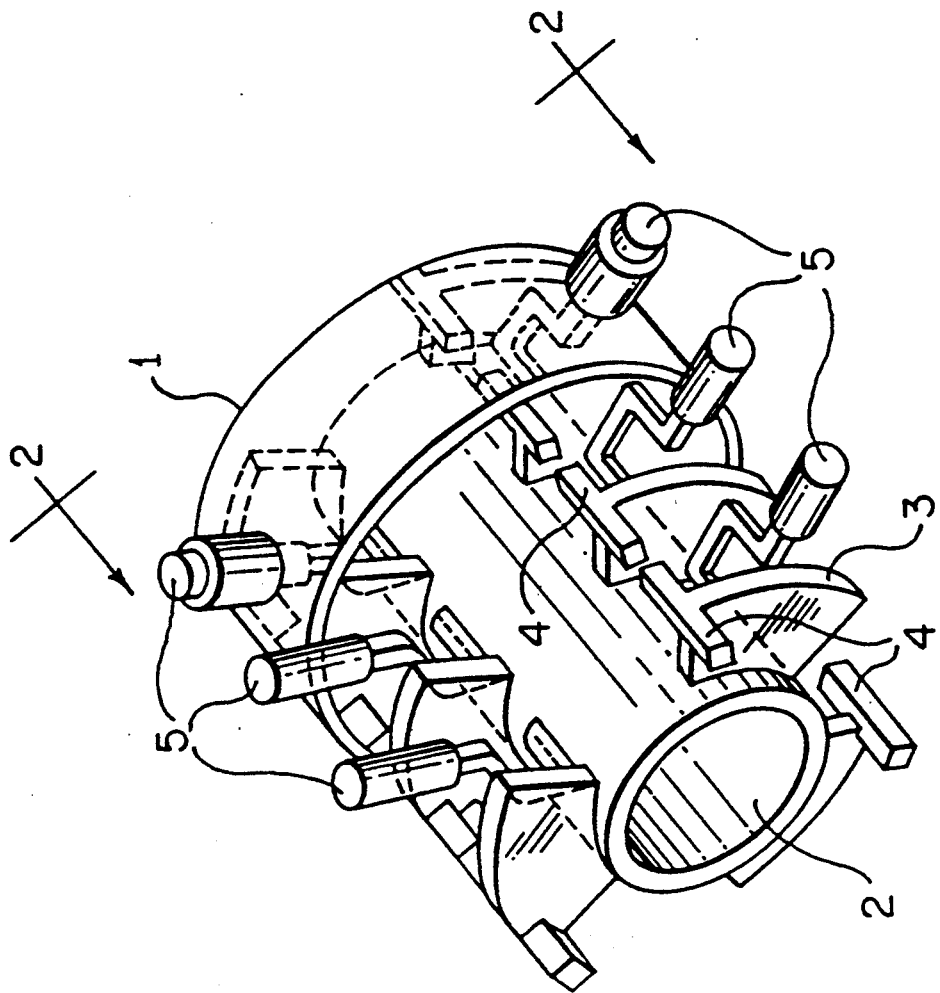

The unit can process materials at temperatures from about −10° C. to about 300° C., using glycol/water, tempered water, pressurized steam, or hot oil as the fluid in the heating/cooling jacket. Practical speed varies with the size of the unit. For a small (1.5 Liter) unit, speeds can vary from about 3 to about 120 rpm. For larger (commercial scale) units, the maximum speed is reduced. The unit is normally suitable for 10 mbar to about 6 bar operating pressure, although it is conceivable that higher pressure ratings could be obtained by specialized construction.

The materials of construction of the reactor can be carbon steel, stainless steel, or Hastelloy, and because of the highly corrosive nature of the compounds used in this application, it is preferred to use Hastelloy B for those surfaces exposed to the reactants.

The process of the present invention comprises the following steps: Before charging the reactor with the reactants a nitrogen sweep might be used to dry the reactor and remove moisture. The nitrogen sweep may be used continuously during the whole process.

The phenylalkyltrichlorosilane or naphthylalkyltrichlorosilane is charged in step (a) to the reactor and while agitating, an essentially equimolar ratio of chlorosulfonic acid is added at a rate sufficient to control foaming of the HCl by product to a manageable level. A slight reduction of pressure may be used in this step of from about 850 to 920 mbar. The temperature in this step ranges from about 20° to about 80° C., preferably from about 20° to about 50° C. When the chlorosulfonic acid addition is complete, the temperature is raised in step (b) to about 80° to 150° C., preferably to about 90° to 120° C. allowing the mixture to react under evolution of HCl, which causes foaming. When the foaming subsides the intermediate becomes more and more viscous to a pasty solid.

Optionally the pressure in the reactor is reduced in step (c) to about 300 to about 20 mbar, preferably to about 200 to about 20 mbar to evaporate the HCl over a time period of from about 10 minutes to about 100 minutes.

If this step (c) is performed, the pressure is increased again to normal, and the agitator speed may be reduced to about 30 to about 20 rpm. In step (d), the solid intermediate is hydrolyzed.

The hydrolysis of the intermediate is performed by adding distilled or demineralized water to the reactor or, preferably, by blowing steam through the reactor, optionally under vacuum. In this step sulfophenylalkylsiloxane or sulfonaphthylalkylsiloxane and HCl as a by-product is formed.

Excess water and the HCl by-product is removed in step (e) by reducing the pressure to about 300 to about 20 mbar, preferably to about 200 to about 20 mbar at a temperature of from about 20° C. to about 95° C., preferably from about 60° C. to about 95° C.

If necessary, the water or steam addition and pressure reduction could be repeated several times to ensure that hydrolysis is complete and HCl is removed.

The pressure is raised to normal and the resulting product is sulfophenylalkylsiloxane or sulfonaphthylalkylsiloxane in form of a powder with a particle size of from 20 to 200 microns.

EXAMPLE 1

First, a nitrogen sweep was used to dry the reactor and remove moisture. To the 770 ml Hastelloy ® B Discotherm laboratory reactor, 279 ml of phenylethyltrichlorosilane was added. The agitator was started at 80 rpm and 88 ml of chlorosulfonic acid dripped in over an 8 minute period with the reactor under a slight vacuum (850 mbar absolute). The temperature was then raised slowly over 35 minutes to about 90° C. As the batch became quite viscous the rpm of the reactor was lowered to about 6 rpm. The temperature remained near 90° C. for another 25 minutes during which time, the pressure was lowered in steps to 500, 300 and then 100 mbar absolute. Cooling was then applied and the batch cooled to 52° C. The cooling separated most of the material from the surfaces of the reactor over a 15 minute period while the reactor temperature continued to fall to 39° C. 37 ml of water were then added to the reactor and the reactor agitated at 70 rpm for 25 minutes under 850 mbar pressure. Higher vacuum of 100 to 120 mbar was applied and held for 15 minutes. 10 ml more water was added and the reactor held at 850 mbar for another 20 minutes. Vacuum of 100 mbar absolute pressure was again applied for another 15 minutes and the product removed.

The off-white to tan, flowable powder analyzed as follow: 0.39 to 0.8% chloride, 2.4 to 2.57% sulfate, 23.2% SiO2 and 353.1 corrected equivalent weight. The adjusted assay which accounted for 8.3% water was 96.0% sulfophenylethylsiloxane.

We claim:

1. A process for preparing a sulfophenylalkylsiloxane or a sulfonaphthylalkylsiloxane having either of the following formulae:

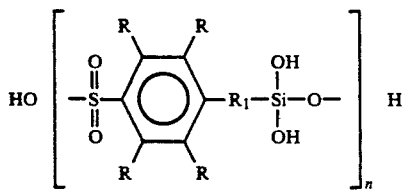 (I)

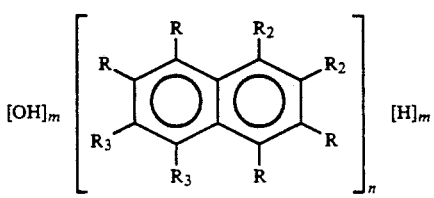 (II)

in a reactor containing a self-cleaning agitator, comprising:

a) adding an essentially equimolar ratio of chlorosulfonic acid to a phenylalkyltrichlorosilane or a naphthylalkyltrichlorosilane having either of the following formulae:

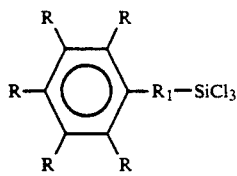 (III)

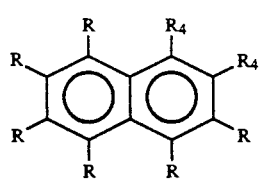 (IV)

wherein R of formulae I,II,III, and IV is individually hydrogen halogen, or an alkyl radical having 1 to 4 carbon atoms; $R_1$ is an alkylene radical having 2 to 5 carbon atoms; $R_2$ is R or

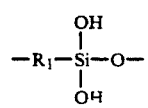

with the proviso that at least one $R_2$ be

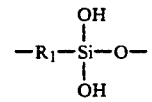

$R_3$ is—H or

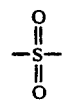

with the proviso that at least one $R_3$ be

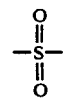

$R_4$ is R or—$R_1SiCl_3$ with the proviso that at least one $R_4$ be—$R_1SiCl_3$ and n is at least 1, m is 1 or 2 in said reactor under agitation at a temperature of from about 20° to about 80° C. and at a rate sufficient to control formation of HCl;

b) raising the temperature up to about 80° to about 150° C. until HCl formation stops and a solid intermediate is formed;

c) optionally reducing the pressure in the reactor to about 300 to about 20 mbar;

d) hydrolyzing the intermediate by adding water at normal pressure in the reactor and at a temperature of from about 20° C. to about 50° C., to form said sulfophenylalkylsiloxane or a sulfonaphthylalkylsiloxane and HCl;

e) reducing the pressure in the reactor to about 300 mbar to about 20 mbar at a temperature of from about 20° C. to about 95° C. until excess water and HCl is removed; and f) removing the dry sulfophenylalkylsiloxane or sulfonaphthylalkylsiloxane from the reactor.

2. The process according to claim 1, wherein the agitator is rotating with a speed of from about 3 to about 120 rpm.

3. The process according to claim 1 wherein the temperature in step b) is from about 90° to about 120° C.

4. The process according to claim 1, wherein the pressure in step (c) is from about 20 to about 200 mbar.

5. The process according to claim 1, wherein the agitator speed is reduced after step (c) to about 3 to about 20 rpm.

6. The process according to claim 1, wherein the hydrolyzing step (d) is performed with steam.

7. The process according to claim 1, wherein the pressure in step (e) is reduced to about 300 to about 20 m bar.

8. The process according to claim 1, wherein steps (d) and (e) are repeated.

9. The process according to claim 1, wherein the sulfophenylalkylsiloxane or sulfonaphthylalkylsiloxane is prepared in form of a powder.

10. The process according to claim 9, wherein the powder has a particle size of from about 20 to about 200 microns.

* * * * *